United States Patent
Amr et al.

(10) Patent No.: US 10,137,138 B1
(45) Date of Patent: Nov. 27, 2018

(54) SULFONYLUREA DERIVATIVES OF OLEANOLIC ACID

(71) Applicant: KING SAUD UNIVERSITY, Riyadh (SA)

(72) Inventors: Abd El-Galil E. Amr, Riyadh (SA); Mohamed A. Al-Omar, Riyadh (SA); Abdulrahman Abdulaziz Almehizia, Riyadh (SA); Ahmed Mohamed Naglah, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 15/991,916

(22) Filed: May 29, 2018

(51) Int. Cl.
  *A61K 31/64* (2006.01)
  *A61P 3/10* (2006.01)
  *A61K 9/00* (2006.01)

(52) U.S. Cl.
  CPC ............ *A61K 31/64* (2013.01); *A61K 9/0053* (2013.01); *A61P 3/10* (2018.01)

(58) Field of Classification Search
  None
  See application file for complete search history.

(56) References Cited

U.S. PATENT DOCUMENTS

| | | |
|---|---|---|
| 7,915,402 B2 | 3/2011 | Anderson et al. |
| 7,943,778 B2 | 5/2011 | Jiang et al. |
| 8,921,419 B2 | 12/2014 | Gribble et al. |
| 8,981,144 B2 | 3/2015 | Griblle et al. |
| 9,156,801 B2 | 10/2015 | Xu et al. |
| 9,856,204 B2 | 1/2018 | Adams et al. |

OTHER PUBLICATIONS

Ahmadi et al., "Synthesis and investigating hypoglycemic and hypolipidemic activities of some glibenclamide analogues in rats," Mini-Reviews in Medicinal Chemistry, 2014, 14: pp. 208-213.
Wang et al., "Antidiabetic Effect of Oleanolic Acid: A Promising Use of a Traditional Pharmacological Agent," Phytotherapy Res., 2011, 25(7): pp. 1031-1040.

*Primary Examiner* — Kamal A Saeed
(74) *Attorney, Agent, or Firm* — Richard C. Litman

(57) ABSTRACT

The sulfonylurea derivatives of oleanolic acid include compounds replacing the 5-chloro-2-methoxybenzoic acid moiety found in glibenclamide with oleanolic acid. The resulting triterpenoidal sulfonylurea derivatives are compounds having the following formula:

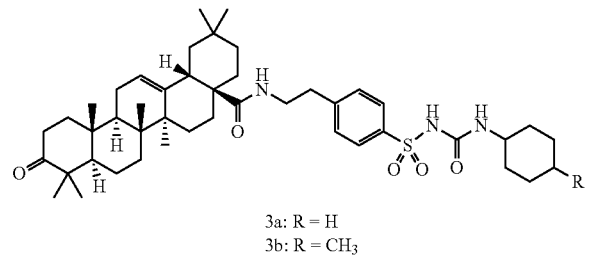

3a: R = H
3b: R = CH$_3$ or a pharmaceutically acceptable salt thereof. The derivatives are synthesized by condensation of 3-oxo-Olean-12-en-28-oic acid with 4-(2-aminoethyl)benzenesulfonamide to form an intermediate product, followed by reaction with cyclohexyl isocyanate or 4-methylcyclohexyl isocyanate to give 3a or 3b, respectively. The sulfonylurea derivative compounds were screened for their oral hypoglycemic activity in vivo using the alloxan-induced diabetic mouse model and proved more potent than either glibenclamide or oleanolic acid.

14 Claims, 2 Drawing Sheets

SULFONYLUREA DERIVATIVES OF OLEANOLIC ACID

BACKGROUND

1. Field

The disclosure of the present patent application relates to compounds exhibiting anti-diabetic activity, and particularly to sulfonylurea derivatives of oleanolic acid.

2. Description of the Related Art

Diabetes mellitus (DM) is a metabolic disorder characterized by chronic hyperglycemia. The American Diabetes Association suggests that by the year 2030, over 350 million people worldwide will be afflicted with this disease and its complications. In Type II DM, a patient's body develops insulin resistance, resulting in hyperglycemia. At present, four types of chemical drugs, including sulfonylureas, biguanides, α-glucosidase inhibitors and euglycemic agents, are used clinically for the treatment of Type 2 DM. Oleanolic acid is a natural triterpenoid, which has been shown to lower blood glucose. The sulfonylureas have been shown to increase insulin release from the pancreas.

Recent developments in anti-diabetic treatment have focused on replacing insulin injections with oral treatment, as well as on increasing the potency and duration of available anti-diabetic agents.

Thus, oleanolic acid sulfonylurea derivatives solving the aforementioned problem are desired.

SUMMARY

The sulfonylurea derivatives of oleanolic acid include compounds replacing the 5-chloro-2-methoxybenzoic acid moiety found in glibenclamide with oleanolic acid. The resulting triterpenoidal sulfonylurea derivatives are compounds having the following formula:

or a pharmaceutically acceptable salt thereof. The derivatives are synthesized by condensation of 3-oxo-Olean-12-en-28-oic acid with 4-(2-aminoethyl)benzenesulfonamide to form an intermediate product, followed by reaction with cyclohexyl isocyanate or 4-methylcyclohexyl isocyanate to give 3a or 3b, respectively. The sulfonylurea derivative compounds were screened for their oral hypoglycemic activity in vivo using the alloxan-induced diabetic mouse model and proved more potent than either glibenclamide or oleanolic acid.

These and other features of the present disclosure will become readily apparent upon further review of the following specification and drawings.

DETAILED DESCRIPTION OF THE PREFERRED EMBODIMENTS

The sulfonylurea derivatives of oleanolic acid include compounds replacing the 5-chloro-2-methoxybenzoic acid moiety found in glibenclamide with oleanolic acid. The resulting triterpenoidal sulfonylurea derivatives are compounds having the following formula:

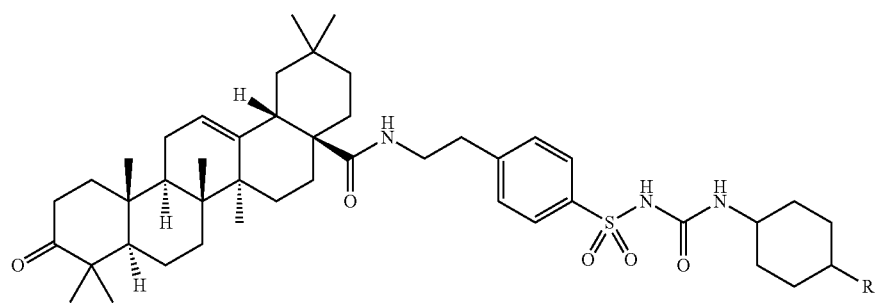

3a: R = H
3b: R = CH$_3$

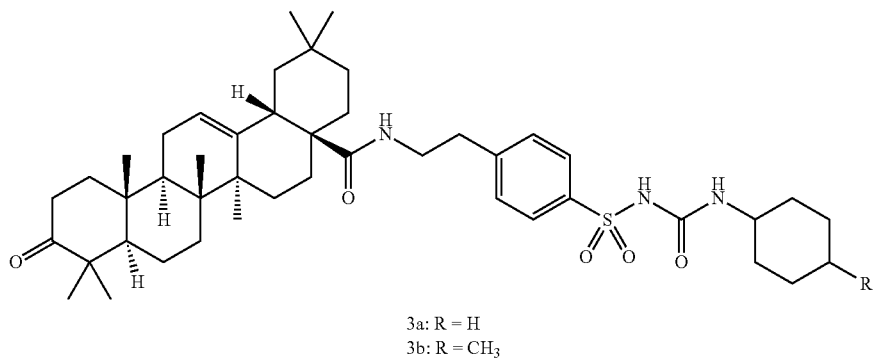

3a: R = H
3b: R = CH$_3$ or a pharmaceutically acceptable salt thereof. The derivatives are synthesized by condensation of 3-oxo-Olean-12-en-28-oic acid with 4-(2-aminoethyl)benzenesulfonamide to form an intermediate product, followed by reaction with cyclohexyl isocyanate or 4-methylcyclohexyl isocyanate to give 3a or 3b. The sulfonylurea derivative compounds were screened for their oral hypoglycemic activity in vivo using the alloxan-induced diabetic mouse model and proved more potent than either glibenclamide or oleanolic acid. The sulfonylurea derivatives of oleanolic acid are therefore believed to be good candidates for the active ingredient of a pharmaceutical composition for oral administration in the treatment of diabetes.

The sulfonylurea derivatives of oleanolic acid will be better understood with reference to the following working examples, in which all melting points are uncorrected and were measured using an electrothermal capillary melting point apparatus. The IR spectra were recorded on a Shimadzu FT-IR 8101 PC infrared spectrophotometer. The $^1$H-NMR spectra were determined with a Bruker AM-500 MHz spectrometer. The chemical shifts are expressed on the δ (ppm) scale using TMS (tetramethylsilane) as the internal reference standard. Mass spectra were recorded on a Finnigan SSQ operating at 70 eV. Elemental analysis was determined on a Perkin Elmer 240 (microanalysis) Microanalysis Center, Cairo University, Cairo, Egypt.

Example 1

Synthesis of Sulfonylurea Derivatives of Oleanolic Acid—General Reaction

Figure 1:
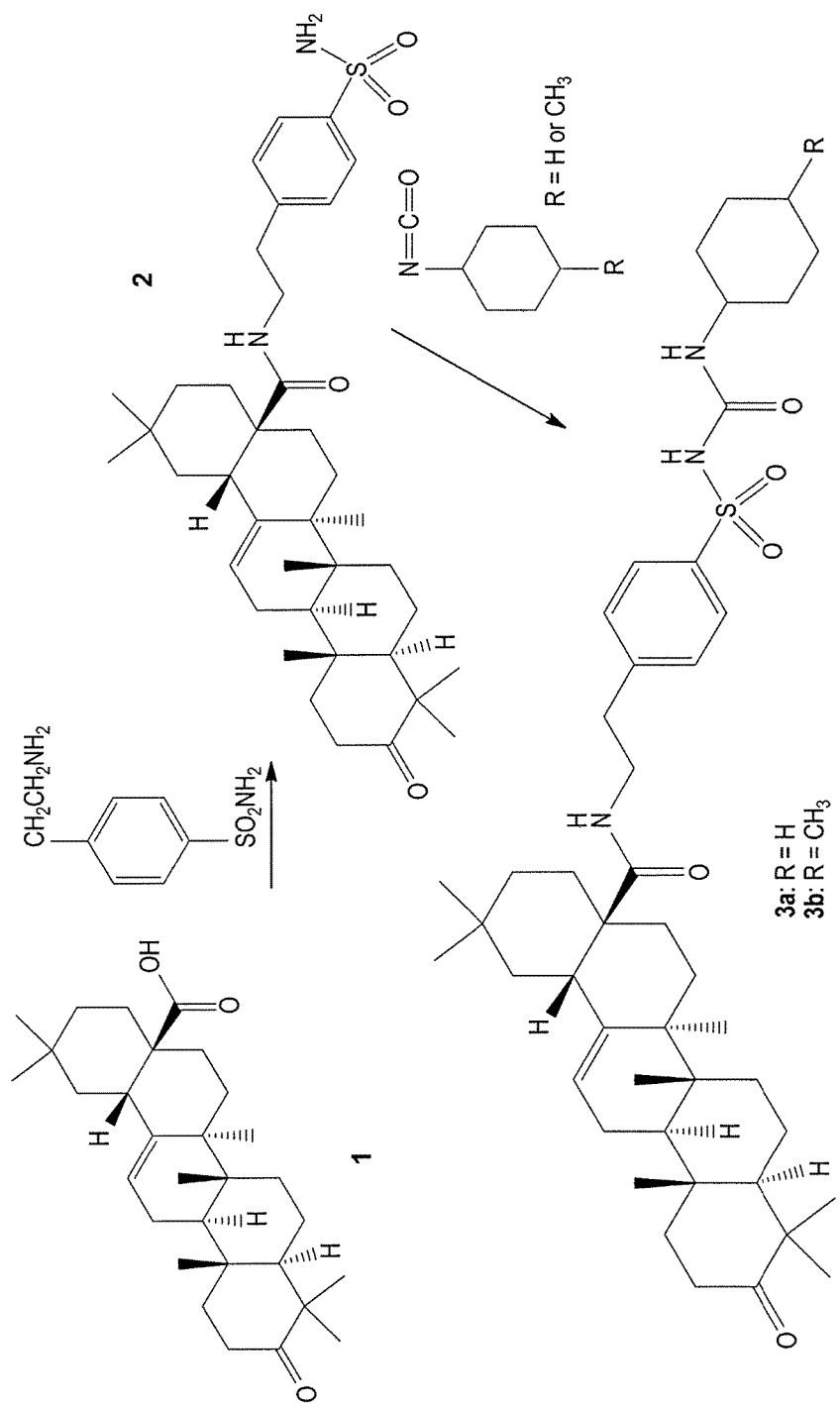
FIG. 1 is a reaction scheme for the synthesis of sulfonylurea derivatives of oleanolic acid as described herein.

An exemplary reaction scheme for preparing the sulfonylurea derivatives of oleanolic acid is shown in FIG. 1. Briefly, N-[(p-ethyl)-benzene-sulfonamide]-3-oxo-18β-olean-12-ene-28-carboxamide (2) is prepared by condensing 3-oxo-Olean-12-en-28-oic acid (1), also referred to a 3-oxo-oleanolic acid, with 4-(2-aminoethyl)benzenesulfonamide using the mixed anhydride technique adopted for the preparation of amides using trifluoroaceticanhydride. Compound 2 is then reacted with cyclohexyl isocyanate or 4-methylcyclohexyl isocyanate to produce the sulfonylurea derivatives 3a and 3b, respectively.

Example 2

Synthesis of Intermediate

In more detail, the intermediate compound, N-[(4-ethyl)-benzenesulfonamide]-3-oxo-18β-olean-12-ene-28-carboxamide (2), was synthesized as follows. Trifluoroaceticanhydride (4 mmol) was added dropwise to a solution of compound 1 (4 mmol) in dioxane (100 ml) at 0-5° C. The resulting mixture was reacted for 1.5 hr, then 4-(2-aminoethyl)benzenesulfonamide (4 mmol) was added, and the resulting mixture was stored without stirring overnight. The reaction mixture was then evaporated under reduced pressure to dryness and the resulting solid product was crystallized from ethyl acetate/methanol to give compound 2. Yield 90%, mp. 287-289° C., $[\alpha]_D^{25}$=+112 (c 1, CHCl$_3$); IR (KBr): 3551-3410 (NH$_2$, NH), 3050 (CH—Ar), 2931 (CH-aliph), 1748 (C=O), 1335 (S=O) cm$^{-1}$. $^1$H NMR (pyridine-d$_5$): δ ppm 0.83 (d, 1H, CH), 0.89 (s, 3H, CH$_3$), 0.93 (s, 3H, CH$_3$), 0.98 (s, 3H, CH$_3$), 1.02 (d, 1H, CH), 1.06 (s, 3H, CH$_3$), 1.11 (s, 3H, CH$_3$), 1.18-1.27 (m, 8H, 2CH and 2CH$_3$), 1.37-1.70 (m, 7H, 7 CH), 1.73-1.75 (m, 2H, CH$_2$, C-2), 1.82-1.98 (m, 6H, 4CH and CH$_2$), 2.02-2.17 (m, 3H, 3CH), 3.37 (d, 1H, CH), 5.59 (s, 1H, CH), 6.71 (s, 1H, CONH) [olean skeleton], 2.62 (t, 2H, CH$_2$), 3.22 (t, 2H, CH$_2$), 5.13 (s, 1H, SONH), 6.14 (s, 1H, CONH), 7.15-7.28 (m, 4H, Ar). $^{13}$C NMR (pyridine-d$_5$): δ ppm 15.54, 16.56, 17.45, 18.64, 23.57, 23.61, 23.65, 26.67, 28.45, 28.48, 28.65, 31.45, 33.41, 33.54, 33.98, 34.68, 37.57, 39.43, 39.67, 39.85, 42.77, 42.83, 46.36, 46.69, 48.64, 55.45, 122.56, 144.74, 177.64, 210.65, (C1-C30) [olean skeleton], 32.24, 48.56 (ethylene bridge), 125.48, 127.23, 139.12, 145.34 (6C, Ar—C). MS (EI): m/z 637 (85%) [M+]. Anal. C$_{38}$H$_{56}$N$_2$O$_4$S (636.93): Found C, 71.60; H, 8.80; N, 4.35; S, 5.00; Calcd C, 71.66; H, 8.86; N, 4.40; S, 5.03.

Example 3

Synthesis of Final Product

In more detail, the final products, N$_1$-[4-(3-oxo-18β-olean-12-ene-28-amido-ethyl)benzenesulfonyl]-N$_2$-cyclohexylurea derivatives (3a,3b) were synthesized as follows. Unsubstituted or substituted cyclohexyl isocyanates, namely, cyclohexyl isocyanate or 4-methylcyclohexyl isocyanate (1.1 mmol), were added dropwise to a solution of compound 2 (1 mmol) in sodium hydroxide (8 ml, 10%) and acetone (20 ml) at 0-5° C. The resulting reaction mixture was kept at the same temperature for 3 hr, diluted with a water/methanol mixture (1:1), and then filtered off. The resulting filtrate was acidified with HCl, and a separated solid was filtered off, dried and recrystallized from acetic acid to yield sulfonylurea derivative compounds 3a or 3b, as follows.

N$_1$-[p-(4-Oxo-18β-olean-12-ene-28-amido-ethyl)-benzenesulfonyl]-N$_2$-cyclohexyl-urea (3a): Yield 81%, mp. 327°

C., $[\alpha]_D^{25}$=+123 (c 1, CHCl$_3$); IR (KBr): 3511-3386 (2NH), 3052 (CH—Ar), 2922 (CH-aliph), 1746 (C=O), 1698-1687 (N—C=O), 1335 (S=O) cm$^{1+}$. $^1$H NMR (pyridine-d$_5$): δ ppm 0.84 (d, 1H, CH), 0.90 (s, 3H, CH$_3$), 0.95 (s, 3H, CH$_3$), 1.00 (s, 3H, CH$_3$), 1.04 (d, 1H, CH), 1.08 (s, 3H, CH$_3$), 1.15 (s, 3H, CH$_3$), 1.20-1.45 (m, 11H, 5CH and 2 CH$_3$), 1.50-1.58 (m, 3H, 3 CH), 1.75-1.95 (m, 7H, 3CH and 2 CH$_2$), 1.98-2.16 (m, 4H, 4 CH), 3.36 (d, 1H, CH), 3.44 (d, 1H, CH), 5.58 (s, 1H, CH), 6.70 (s, 1H, CONH) [Olean Skeleton], 1.11-1.13 (m, 5H, CH), 1.62-1.64 (m, 5H, CH), 3.18-3.20 (m, 1H, CH), 2.60 (t, 2H, CH$_2$), 3.20 (t, 2H, CH$_2$), 5.15 (s, 1H, SONH), 6.10 (s, 1H, CONH), 7.17-7.25 (m, 4H, Ar). $^{13}$C NMR (pyridine-d$_5$): δ ppm 15.69, 16.47, 17.76, 18.60, 23.51, 23.60, 23.67, 26.54, 28.45, 28.46, 28.85, 31.65, 33.46, 33.67, 33.74, 34.45, 37.56, 39.56, 39.58, 39.85, 42.77, 42.80, 46.36, 46.89, 48.44, 55.56, 144.79, 122.56, 177.45, 210.24 [30C, Olean Skeleton], 28.12, 34.40, 25.01, 25.39 [6C, cyclohexyl ring], 32.29, 48.70, (2C, CH$_2$CH$_2$), 166.70 (C=O), 125.40, 127.20, 139.10, 145.30 (6C, Ar—C). MS (EI): m/z 762 (100%) [M+]. Anal. C$_{45}$H$_{67}$N$_3$O$_5$S (762.09): Found C, 70.82; H, 8.80; N, 5.45; S, 4.16. Calcd C, 70.92; H, 8.86; N, 5.51; S, 4.21.

N$_1$-[4-(3-Oxo-18β-olean-12-ene-28-amido-ethyl)-benzenesulfonyl]-N$_2$-(4-methylcyclohexyl)-urea (3b): Yield 79%, mp. 200, $[\alpha]_D^{25}$=+106 (c 1, CHCl$_3$); IR (KBr): 3523-3395 (2NH), 3048 (CH—Ar), 2932 (CH-aliph), 1747 (C=O), 1690-1680 (N—C=O), 1331 (S=O) cm$^{-1}$. $^1$H NMR (pyridine-d$_5$): δ ppm 0.87 (d, 1H, CH), 0.91 (s, 3H, CH$_3$), 0.96 (s, 3H, CH$_3$), 1.02 (s, 3H, CH$_3$), 1.07 (d, 1H, CH), 1.10 (s, 3H, CH$_3$), 1.14 (s, 3H, CH$_3$), 1.22-1.46 (m, 11H, 5CH and 2 CH$_3$), 1.50-1.56 (m, 3H, 3CH), 1.67-1.89 (m, 5H, 3 CH and CH$_2$), 1.93-2.05 (m, 5H, 3 CH and CH$_2$), 2.12 (t, 1H, CH), 2.15-2.17 (m, 1H, CH), 3.30 (d, 1H, CH), 5.60 (s, 1H, CH), 6.75 (s, 1H, CONH) [Olean Skeleton], 0.78 (s, 3H, CH$_3$), 0.84 (m, 2H, CH), 1.12 (m, 1H, CH), 1.16-1.18 (m, 3H, 3 CH), 1.58-1.60 (m, 3H, 3 CH), 3.20-3.22 (m, 1H, CH), 2.68 (t, 2H, CH$_2$), 3.12 (t, 2H, CH$_2$), 5.13 (s, 1H, SONH), 6.10 (s, 1H, CONH), 7.18-7.28 (m, 4H, Ar). $^{13}$C NMR (pyridine-d$_5$): δ ppm 15.45, 16.90, 17.67, 18.45, 23.42, 23.45, 23.87, 26.89, 28.67, 28.78, 28.80, 31.56, 33.54, 33.65, 33.76, 34.76, 37.67, 39.45, 39.54, 39.67, 42.45, 42.65, 46.43, 46.56, 48.65, 55.43, 122.45, 144.65, 177.56, 210.65 [30C, Olean Skeleton], 22.7, 28.20, 33.10, 34.60, 36.40 [6C, cyclohexyl ring], 32.56, 48.77 (2C, CH$_2$CH$_2$), 166.78 (C=O), 125.47, 127.26, 139.11, 145.38 (6C, Ar—C). MS (EI): m/z 776 (100%) [M+]. Anal. C$_{46}$H$_{69}$N$_3$O$_5$S (776.12): Found C, 71.19; H, 8.96; N, 5.41; S, 4.13. Calcd C, 71.10; H, 8.90; N, 5.35; S, 4.10.

Example 4

Evaluation of In Vivo Oral Hypoglycemic Activity

Figure 2:
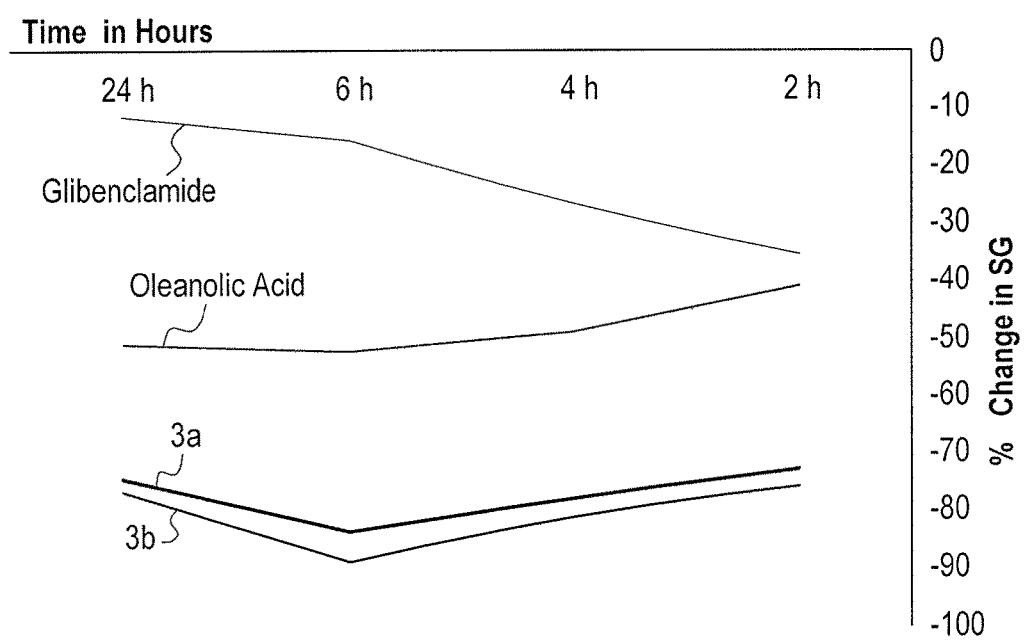
FIG. 2 is a graph illustrating the percentage change in blood glucose (BG) in diabetic mice after administration of glibenclamide, oleanolic acid, and compounds 3a and 3b (200 μg/kg body weight, acute study).

The sulfonylurea derivatives of oleanolic acid were screened for their oral hypoglycemic activity in vivo using the alloxan-induced diabetic mouse model. In an acute evaluation, the percentage change in blood glucose levels in diabetic mice after oral administration of the test compounds (200 μg/kg body weight) was measured and summarized in Table 1 and FIG. 2.

Briefly, animals were fasted overnight and the fasting blood glucose (BG) (0 hour) levels were calculated. Test and control compounds were administered at a fixed dose of 200 μg/kg body weight orally (homogenized suspension in 0.5% carboxymethyl cellulose (CMC) and permissible amounts of Tween 80). Animals in the vehicle-treated group were given an equal volume of 0.5% CMC and control group animals were untreated. Blood samples were removed from all animals at 2, 4, 6 and 24 hours and the percentage change in BG was calculated. The data were analyzed by one-way ANOVA followed by Dunnett's test. The results were expressed as mean±standard error of mean for each group, n=6 for each group, and p<0.01 or p<0.05 was considered as statistically significant. As illustrated in Table 1 and FIG. 1, the sulfonylurea derivative compounds showed a more potent anti-diabetic activity and a longer duration of action than the reference anti-diabetic drugs, glibenclamide and oleanolic acid.

TABLE 1

Acute Evaluation of in vivo Hypoglycemic Activity (% change in BG)

| | 2 h | 4 h | 6 h | 24 h |
|---|---|---|---|---|
| Control | 1.21 ± 0.32 | 2.11 ± 0.32 | 2.45 ± 0.22 | −0.21 ± 0.2 |
| Vehicle | 5.09 ± 0.32 | 9.87 ± 0.43 | 9.89 ± 0.32 | 1.51 ± 0.2 |
| Glibenclamide | −35.55 ± 1.55 | −26.54 ± 1.32 | −15.58 ± 0.88 | −11.24 ± 0.11 |
| Oleanolic acid | −40.79 ± 1.20 | −48.66 ± 1.31 | −52.17 ± 1.31 | −51.01 ± 1.11 |
| 3a | −72.76 ± 0.78 | −77.76 ± 0.90 | −83.56 ± 0.83 | −74.44 ± 0.74 |
| 3b | −75.56 ± 0.86 | −80.97 ± 0.92 | −88.89 ± 0.98 | −76.76 ± 0.89 |

The sulfonylurea derivative compounds were also screened for their oral hypoglycemic activity after several days of administration using the alloxan-induced diabetic mouse model, and percentage changes in blood glucose levels after oral administration (200 g/kg body weight) were recorded (Table 2).

Briefly, animals were fasted overnight, and the fasting BG (0 day) levels were calculated. Test and control compounds were administered orally for 21 days at a fixed time and a fixed dose of 200 μg/kg body weight (homogenized suspension in 0.5% CMC and permissible amounts of Tween 80). After 21 days, treatment was stopped and animals were rested for a period of 7 days. Animals in the vehicle-treated group were then given an equal amount of 0.5% CMC and those of control group were untreated. Blood samples were removed from all animals throughout the course of the study at 7, 14, 21 and 28 days, and percentage change in BG was calculated. The data were analyzed by one-way ANOVA, followed by Dunnett's test. The results were expressed as mean±standard error of mean for each group, n=6 for each group, and p<0.01 or p<0.05 was considered as statistically significant (Table 2). The sulfonylurea derivative compounds showed several times more potent anti-diabetic activity than the reference anti-diabetic drugs, glibenclamide and oleanolic acid.

TABLE 2

Sub-Acute Evaluation of in vivo Hypoglycemic Activity (% change in BG)

| Comp. No | 7 day | 14 day | 21 day | 7 days rest period |
|---|---|---|---|---|
| Control | 1.2 | 1.34 | 1.45 | 1.67 |
| Vehicle | 6.45 | 7.65 | 8.76 | 9.87 |
| Glibenclamide | −16.23 ± 0.32 | −22.57 ± 0.54 | −30.87 ± 0.58 | −28.48 ± 0.58 |
| Oleanolic acid | −10.56 ± 0.80 | −20.35 ± 0.72 | −37.68 ± 0.78 | −30.32 ± 0.83 |
| 3a | −76.87 ± 0.89 | −80.09 ± 0.90 | −87.65 ± 0.95 | −81.78 ± 0.90 |
| 3b | −80.80 ± 0.80 | −84.98 ± 1.16 | −88.89 ± 1.12 | −82.12 ± 1.17 |

It is to be understood that the oleanolic acid sulfonylurea as an anti-diabetic is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A sulfonylurea derivative of oleanolic acid, comprising a compound having the formula:

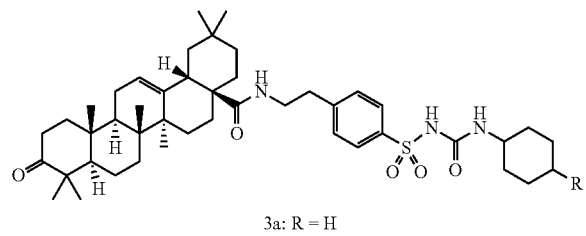

where R is selected from the group consisting H and CH$_3$, or a pharmaceutically acceptable salt thereof.

2. The sulfonylurea derivative of oleanolic acid according to claim 1, wherein R is H.

3. The sulfonylurea derivative of oleanolic acid according to claim 1, wherein R is CH$_3$.

4. A pharmaceutical composition, comprising an effective amount of a compound of claim 1 and a pharmacologically acceptable carrier.

5. The pharmaceutical composition according to claim 4, wherein the effective amount of said compound is 200 µg/kg body weight.

6. The pharmaceutical composition according to claim 4, wherein the composition is formulated for oral administration.

7. The pharmaceutical composition according to claim 4, wherein the composition is a suspension formulated for oral administration.

8. A method of reducing blood glucose in a diabetic patient, comprising administering an effective amount of a compound of claim 1 to the patient.

9. A method for achieving an effect in a diabetic patient, comprising administering an effective amount of a compound of claim 1 to the patient, wherein the effect is lowering blood glucose.

10. A method of making a sulfonylurea derivative of oleanolic acid, comprising the steps of:

condensing 3-oxo-Olean-12-en-28-oic acid with 4-(2-aminoethyl)benzenesulfonamide to obtain N-[(4-ethyl)-benzenesulfonamide]-3-oxo-18β-olean-12-ene-28-carboxamide as an intermediate product; and reacting the intermediate product with a cyclohexyl isocyanate to obtain a sulfonylurea derivative of oleanolic acid having the formula:

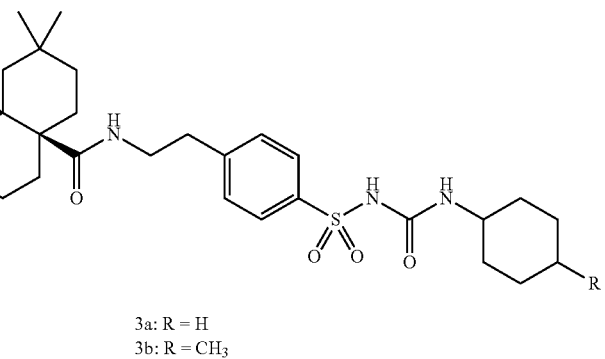

wherein R is hydrogen of methyl.

11. The method of making a sulfonylurea derivative of oleanolic acid according to claim 10, wherein the cyclohexyl isocyanate is unsubstituted cyclohexyl isocyanate, whereby R is hydrogen.

12. The method of making a sulfonylurea derivative of oleanolic acid according to claim 10, wherein the cyclohexyl isocyanate is methylcyclohexyl isocyanate, whereby R is methyl.

13. The method of making a sulfonylurea derivative of oleanolic acid according to claim 10, wherein the step of condensing 3-oxo-Olean-12-en-28-oic acid with 4-(2-aminoethyl)benzenesulfonamide comprises:

adding an equimolar amount of trifluoroaceticanhydride dropwise to a solution of 3-oxo-Olean-12-en-28-oic acid in dioxane at a temperature between 0 and 5° C. to form a reaction mixture;

adding an amount of 4-(2-aminoethyl)benzenesulfonamide equimolar to the trifluoroaceticanhydride and equimolar to the 3-oxo-Olean-12-en-28-oic acid to the reaction mixture;

storing the reaction mixture overnight without stirring evaporating the stored reaction mixture to dryness to obtain a precipitate; and recrystallizing the precipitate in ethyl acetate/methanol.

14. The method of making a sulfonylurea derivative of oleanolic acid according to claim 13, wherein the step of reacting the intermediate product with a cyclohexyl isocyanate comprises:

adding a substantially equimolar amount of the cyclohexyl isocyanate dropwise to a solution of the intermediate product in 8% sodium hydroxide and acetone at a temperature between 0 and 5° C. to form a reaction mixture;

maintaining the reaction mixture at a temperature between 0 and 5° C. for about three hours;

thereafter, diluting the reaction mixture with a 1:1 mixture of water and methanol;

filtering the diluted reaction mixture;

acidifying the filtrate from the filtered, diluted reaction mixture with hydrogen chloride to obtain a precipitate; and recrystallizing the precipitate in acetic acid to obtain the a sulfonylurea derivative of oleanolic acid.

\* \* \* \* \*